United States Patent [19]

Lundbäck

[11] Patent Number: 4,646,747
[45] Date of Patent: Mar. 3, 1987

[54] ELECTRODE FOR ELECTROCARDIOGRAPHIC EXAMINATIONS

[75] Inventor: Stig Lundbáck, Vaxholm, Sweden
[73] Assignee: Astra-Tech Aktiebolag, Sweden
[21] Appl. No.: 665,023
[22] Filed: Oct. 26, 1984
[30] Foreign Application Priority Data Oct. 28, 1983 [SE] Sweden ................................ 8305947

[51] Int. Cl.$^4$ ................................................ A61B 5/04
[52] U.S. Cl. ........................................ 128/643; 128/802
[58] Field of Search .................. 128/643, 639–640, 128/641, 802–803

[56] References Cited

U.S. PATENT DOCUMENTS

| | | | |
|---|---|---|---|
| 2,580,628 | 1/1952 | Welsh | 128/643 |
| 2,880,729 | 4/1959 | Kruse | 128/643 |
| 3,490,442 | 1/1970 | Streu | 128/643 |
| 3,505,993 | 4/1970 | Lewes et al. | 128/643 |
| 3,534,733 | 10/1970 | Phipps et al. | 128/643 |
| 3,640,270 | 2/1972 | Hoffman | 128/643 |
| 4,137,909 | 2/1979 | Hix | 128/641 |
| 4,166,457 | 9/1979 | Jacobsen et al. | 128/639 |
| 4,217,908 | 8/1980 | Staver | 128/643 |
| 4,235,241 | 11/1980 | Tabuchi et al. | 128/639 |
| 4,248,243 | 2/1981 | Niess et al. | 128/696 |
| 4,369,793 | 1/1983 | Staver et al. | 128/643 |
| 4,469,105 | 9/1984 | Staver | 128/643 |

FOREIGN PATENT DOCUMENTS 248608 8/1966 Austria .

Primary Examiner—Lee S. Cohen
Assistant Examiner—Angela D. Sykes
Attorney, Agent, or Firm—Brumbaugh, Graves, Donohue & Raymond

[57] ABSTRACT

An electrode for electrocardiographic examinations comprises a substantially rigid back piece, an electrode plate joined substantially non-movably to the back piece and a resiliently deformable sealing component interposed between the electrode plate and the back piece. When the electrode is not applied to the patient, flow of ambient air to a vacuum chamber in the back piece is blocked or restricted. Upon applying the electrode to the patient's skin, an outer sealing rim in engagement with the patient's skin forms a seal between the patient's skin and the back piece, thereby to define a vacuum chamber between the back piece and the patient's skin. The vacuum holds the electrode plate firmly in engagement with the patient's skin.

15 Claims, 3 Drawing Figures

ELECTRODE FOR ELECTROCARDIOGRAPHIC EXAMINATIONS

BACKGROUND OF THE INVENTION

The present invention relates to an electrode, especially for examinations by electrocardiography (ECG), of the type that is fastened to the patient's skin by vacuum generated in a cup-like chamber pressed against the skin.

In practice, two main types of electrodes are used at present. On one hand there are disposable electrodes which are fastened by adhesive means (adhesive paste, tape, etc.) or with rubber bands and the like. On the other hand there are multiple-use electrodes working with locally generated vacuum. An old vacuum-based fastening principle uses compressed and thereafter expanding (squeezable) rubber balls, which, however, because of the limited reservoir size are prone to come loose even if there is only the slightest leakage and which, therefore, give rise to appreciable difficulties, e.g., if there are six electrodes to be used simultaneously with a single patient, as is common in clinical routine. None of these systems is thus completely satisfactory.

An electrode that is attached with the aid of vacuum supplied via a flexible tube, and where a valve for this vacuum is closed when the electrode is not attached, opening automatically on application and closing automatically if the electrode comes loose and falls off, is known from Austrian Patent Specification No. 248 608. According to a particular embodiment described in that patent, a spring-loaded electrode plate is connected to a sealing ring by way of an elastic membrane. When the electrode plate is pressed against the skin of a patient, a valve opens and vacuum is generated in a chamber around the electrode, this chamber being defined by the sealing ring. Unfortunately, the movability of the electrode plate in relation to the sealing ring via a membrane can result in a bad fit of the electrode to the skin because the electrode plate can both tilt and move axially relative to the sealing ring by means of the elastic membrane, unless high negative pressures of the sort leaving marks on the skin are used. There is, furthermore, no guarantee for the pressure of the electrode on the skin to be constant, causing the proper electrical functioning of the electrode to be dependent on the patient being at rest. Very small movements of the electrode are accompanied by changes in contact resistance, causing the baseline against which the ECG-variable is recorded to lack in definition and to become variable. The fixation by vacuum with a single vacuum source for many electrodes, although being advantageous from a theoretical standpoint, for practical purposes has, therefore, not come into common use.

An electrode which is kept in place by vacuum and which has a surrounding sealing ring connected in a relatively rigid way to a centrally located electrode plate is known from U.S. Pat. No. 4,248,243. This electrode cannot, however, be kept under vacuum by connection to a central vacuum source, because it is lacking the self-closing valve described in the above-referred to Austrian patent specification. The electrode of U.S. Pat. No. 4,248,243 is fed with pressurized air, which drives an ejector pumping device mounted in the electrode. This means that the electrode is very disturbing to a patient during examination, because the ejector device makes a hissing or whizzing sound. Moreover, material from the electrode vacuum chamber is blown into the air through the ejector nozzle, such material including constituents of the electrode paste used with the electrode and non-sterile body fluids formed by sweating, which thus gives rise to sanitary problems. Because of its specific design, this electrode can be sterilized only with difficulty, and it is impractical to use it as a disposable electrode. It is further to be noted that relatively high positive pressures have to be supplied, about 0.6 kg per $cm^2$, causing greater sealing difficulties and requiring the use of pressure hose.

SUMMARY OF THE INVENTION

One object of the present invention is to provide an electrode of the vacuum type which becomes firmly attached to the patient, thus making it possible for the patient to move during the ECG-examination, and minimizing variations of the base-line because of changes in contact pressure. The electrode of the present invention enables the heart function in patients to be examined during physical exercise, something which is very desirable from a diagnostic standpoint but which is difficult to carry out and has not been introduced into commonly used clinical routine.

There is provided, in accordance with the present invention, an electrode for electrocardiographic examination and the like comprising a substantially rigid back piece having a chamber adapted to be connected to a vacuum source, an electrode plate joined substantially non-movably to the back piece and having an electrically conductive frontal surface adapted to be connected to a measuring device and to engage the skin of a patient being examined, and a sealing component interposed between the electrode plate and the back piece. The sealing component includes a central portion that is in sealing engagement with the back piece externally of the back piece chamber and a resiliently deformable sealing ring portion extending outwardly from the central portion. The sealing ring portion has an outer sealing rim engageable with the skin of a patient to be examined and with a back piece. The sealing ring portion is adapted to be resiliently deformed by the force on the outer sealing rim when the electrode is pushed toward the patient's skin, whereupon a vacuum is generated in a zone defined by the back piece, the outer sealing rim and the patient's skin inwardly of the outer sealing rim, thus firmly to engage and hold the electrode plate against the patient's skin by a force generated by the vacuum that displaces the back piece, the central portion of the sealing component and the electrode plate toward the patient's skin. When the electrode is not in place on a patient, conduction of ambient air to the back piece chamber is blocked or restricted, preferably by an inner sealing rim on the sealing ring portion of the sealing component that is resiliently engageable with the electrode plate in the absence of an external force applied to the sealing ring portion toward the back piece and that defines with the electrode plate a valve for closing the back piece chamber.

In a preferred embodiment, an electrode, according to the present invention, includes one or more of the following features:

(1) the electrode plate is detachably joined to the back piece, such as by a snap fastener that includes a stem;

(2) the central portion of the sealing component has a hole that removably receives the stem, whereby the center portion of the sealing component is held in a fixed position radially and axially of the stem;

(3) the sealing ring portion of the sealing component includes an annular rib engageable with the back piece and adapted to be deflected upon displacement of the back piece relative to the ring portion;

(4) there is at least one hole in the sealing ring portion of the sealing component between the inner and outer sealing rims for communication of vacuum to the zone between the sealing ring portion and the back piece when the electrode is applied to a patient;

(5) the zone of engagement between the outer sealing rim and the patient's skin is farther from the back piece than is the zone of engagement of the frontal surface of the electrode plate with the patient's skin, whereby the patient's skin is pulled by the vacuum into an convex shape within the outer sealing rim;

(6) the frontal surface of the electrode plate is concave;

(7) the frontal surface of the electrode plate has a multiplicity of small protuberances.

The present invention may be put into practice as a device intended to be partially disposable or as one with easily exchangeable parts which can be sterilized. For example, the electrode plate can be a disposable small "button," because the material best suited for the electrode surface for electrochemical reasons is silver with a layer of silver chloride, which is blackened by light. An electrode may, therefore, be provided with a very thin silver layer. The sealing component can be made from an elastomer and changed after each use, whereafter the used components may be collected, washed and sterilized, unless one decides to dispose of them after one use.

For a better understanding of the invention reference may be made to the following description of an exemplary embodiment, taken in conjunction with the accompanying drawing.

DESCRIPTION OF THE EMBODIMENT

Figure 1:
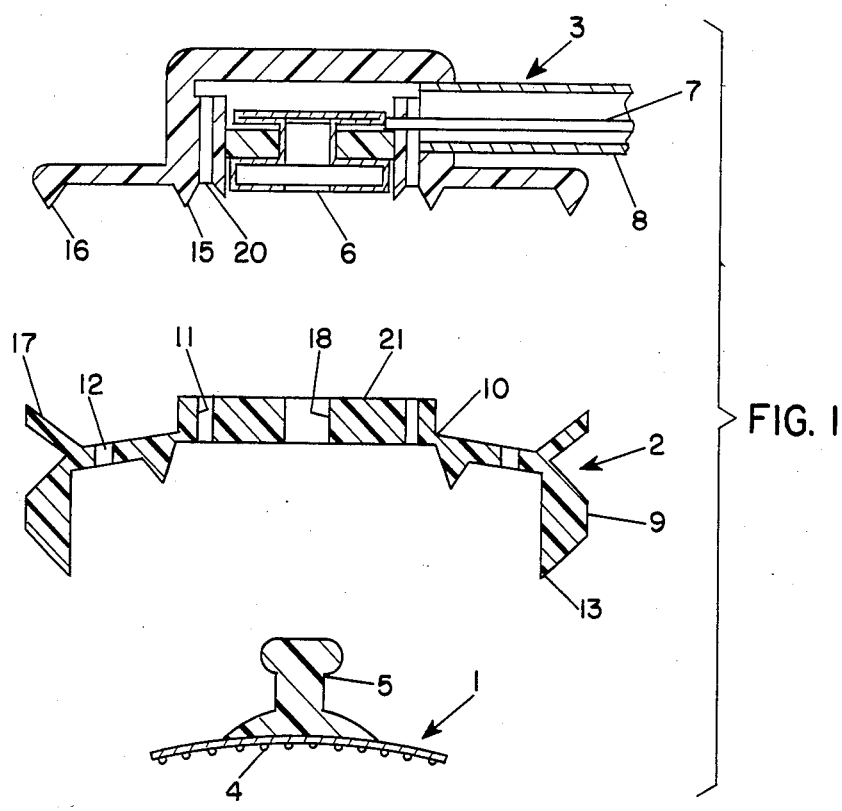
FIG. 1 is an exploded side cross-sectional view of the embodiment taken along a bisecting plane.

The embodiment includes an electrode plate 1, which may be made of metal or plastic, but has a metallic electrically conductive frontal surface 4, such as a layer of silver chloride. The frontal surface of the embodiment is concave, but it can also be flat, and has a multiplicity of small protuberances to give good contact, especially in case of hair growth on the skin. On the back side, there is a stem 5 having an enlarged head, which is the male part of a snap fastener connection. The stem is fastened to the female part 6 of the snap fastener mounted in a back piece 3 after passing through a hole 18 in a sealing component 2, which comprises a sealing ring portion 9. The snap fastener may be of a common button type used in clothing. The back piece 3 may be made from non-conducting plastic provided with metallic shielding (not shown). A flexible vacuum tube 8 is connected to the back piece, and a shielded conductor 7 passes through the tube and is connected to the metallic snap fastener part 6. When the snap fastener is connected, the electrode plate is rigidly connected with the back piece and has, by means of the conductor 7, a connection to measuring equipment (not shown) of known design. The flexible vacuum tube is connected with a chamber in the back piece, and around the snap fastener part 6 there are a number of holes 20. In the embodiment, components 1 and 2 are rotationally symmetrical, which simplifies manufacture but is not absolutely necessary.

The sealing component 2, which is preferably made from silicone rubber, has a disc-like center portion 21 and an annular sealing rim portion 9 of generally L-shaped cross section joined at a juncture 10 to the center portion. The center portion 21 is held axially and radially in fixed position by reception of the stem 5 on the electrode member in the hole 18 (see FIG. 2) and bears against a sealing rim 15 on the back piece 3. The frontal side of the sealing component is connected to the back side through circularly arranged holes 11. A sealing rim 14 on the frontal side of the sealing rim portion 9 bears against the back of the electrode plate 1 in the passive condition of the device (i.e., when no external force acts on the ring portion 9 in a direction toward the back piece 3), and both rim 14 and rim 15 will seal off an evacuated chamber 22 defined by the center portion of the sealing component 2 and the electrode plate 1, this sealed condition resulting from the resiliency of sealing component, which is shaped and dimensioned to achieve the condition shown in FIG. 2. A sealing rib 17 on the component 2 bears resiliently on a rib 16 on the back piece 3, which contributes to this attainment of the closed condition of the chamber 22. Thus, a vacuum applied through the tube 8 is communicated from the chamber in the back piece through the holes 20 and 11 to the chamber 22.

Figure 2:
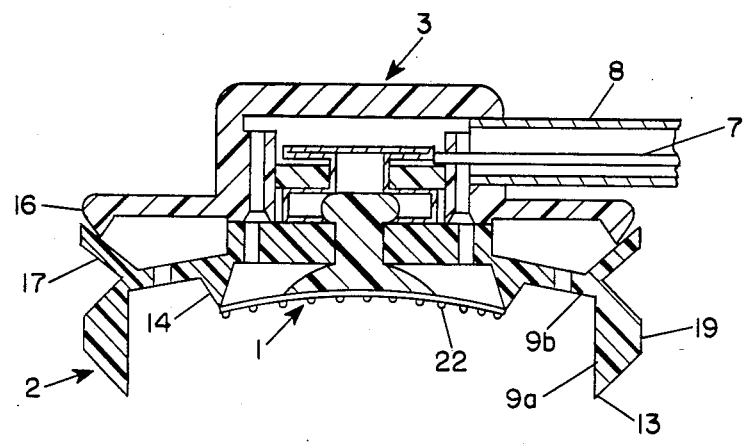
FIG. 2 is a side cross-sectional view of the embodiment showing the configuration when it is not applied to the patient.
Figure 3:
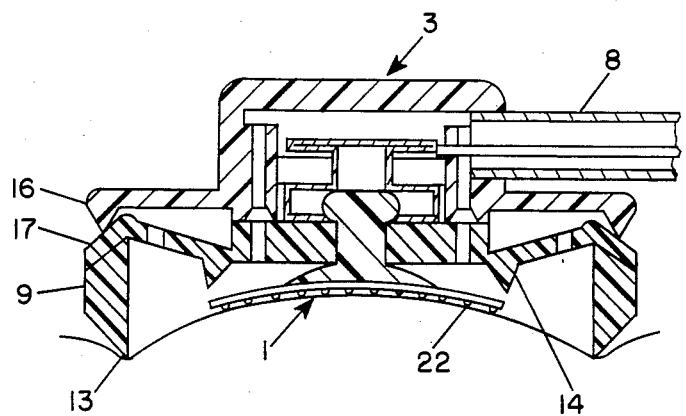
FIG. 3 is a side cross-sectional view of the embodiment showing the configuration when it is applied to the patient.

When the electrode, in the condition shown in FIG. 2, is applied to the skin of a patient (after application of electrode paste), the resisting force from the skin acting on the tip 13 of the sealing ring portion 9 will produce deformation and deflection of the portion 9, consisting mainly of bending up of the ring portion at the juncture 10 with the center portion 21, bending of the rib 17, and bending at the juncture between the outer leg or flange 9a and the inner leg 9b of the L-shaped sealing ring portion 9 (see FIG. 3). Such deformation and deflection unseats the inner sealing rim 14 of the sealing component from the electrode plate 1, thereby communicating the vacuum to the zone or chamber bounded by the flange 9a and to the skin area of the patient within the outer sealing rim 13. The vacuum communicates through the holes 12 in the leg 9b of the sealing ring portion to the zone between the back piece and the leg 9b. Thus, the various zones between the back piece 3 and the patient's skin within the flange 9 are subject to the vacuum. The force on the back piece due to the pressure difference between the ambient air and the vacuum pulls the back piece and the electrode plate toward the skin. A similar pressure difference on the patient's skin pulls the skin into engagement with the electrode plate.

From FIG. 3, it is evident that the back piece 3 and the sealing ring portion 9 are working in the axial direction as an integrated, rigid unit, although an elastic deforming force through flange 17 acts partly radially in respect to back piece 3 on the flange 9a, this deforming force though being negligible in comparison with the pneumatic forces. The vacuum applied does not need to exceed 0.1 kg per cm². The air pressure exerts a force on the electrode against the skin over the area delimited by the sealing rim 13. This force is counteracted by a force from the skin, which is pulled outwardly and in major part is exerted against the frontal surface of the electrode plate, this leading to a particularly good contact. Deformation of the skin also gives rise to a certain contour-sealing effect, which prevents sliding. Electrode paste and perspiration have a tendency to reduce friction, which makes this contour-sealing effect a necessary prerequisite against breaking-off and shearing load forces. An applied breaking-off force will actually lead to the skin complying with that deformation until it becomes too large and rim 13 is no longer sealing, at which stage the electrode, of course, loosens its hold and rim 13 resiles and the configuration shown in FIG. 2 with valve closing results. To achieve proper working it is thus necessary for the electrode surface 4 in the configuration shown in FIG. 3 to be set back in relation to rim 13 of ring 9. With a rim diameter of 30 mm, a suitable set back is 3-4 mm.

The above-described embodiment has many advantages over prior devices. The attachment of, for example, six electrodes to a patient is done very quickly, in that no valves have to be opened, by suitably fastening the electrodes one by one on the body by mere pressing (the electrodes suitably being provided with identifying symbols on the back side of the respective back piece). Hairy skin does not provide any difficulties, and the patient may exercise (e.g., jumping) without the electrodes loosening their hold. Because of the low negative pressure—a tenth of an atmosphere is sufficient—there are no marks formed on the average patient, except for a small red ring where rim 13 has made contact, even if the electrode has been kept attached for half an hour.

After use and disconnection from the vacuum source the only things that have to be done to get the electrodes ready to use on another patient are to remove the electrode plate 1 from the snap connection, whereby the elastomer component 2 also comes off, and to attach new or sterilized parts to the back piece. Sterilization is simple and can be carried out with great numbers of parts simultaneously. The invention is, therefore, extraordinarily practical and hygienic, and makes possible medical examinations which hitherto, because of difficulties with the proper working of the electrodes, have not been possible to carry out in a routine way. By the electrical contact being dependable and stable, examinations may be carried out faster, and the cumbersome sampling methods earlier in use may be shortened. Especially if the electrode is to be used for a longer period of time, or in examinations which involve physical exercise, it may be appropriate to mount some liquid-absorbing material inside the electrode, e.g., a filter paper disc, or the like, which can be laid in between the elastomer element and the back piece, and which may be disposed of after use.

The above-described embodiment includes a valve in the form of the displaceable inner rim 14 for holding a vacuum in the back piece chamber when the electrode is not applied to the patient. While that arrangement is preferred, it is not required. Instead, the passage of air to the back piece chamber can be restricted by making the holes 20 in the back piece or the hole or holes 11 in the sealing component small. The size of the vacuum pump will have to be chosen with regard for controlled leakage of air into the vacuum system.

I claim:

1. An electrode for electrocardiographic examinations and the like comprising a substantially rigid back piece having a chamber, means for connecting the chamber to a vacuum source, an electrode plate joined substantially non-movably to the back piece and having an electrically conductive frontal surface adapted to be connected to a measuring device and adapted to engage the skin of a patient being examined, and a sealing component interposed between the electrode plate and the back piece and having a central portion in sealing engagement with the back piece externally of the back piece chamber and a resiliently deformable sealing ring portion outwardly of the central portion that includes an outer sealing rim engageable with the skin of a patient to be examined and with the back piece, the sealing ring portion being adapted to be resiliently deformed toward the back piece by the force on the outer sealing rim when the electrode is pressed toward the patient's skin, whereby a vacuum is generated in a zone defined by the back piece, the outer sealing rim and the patient's skin inwardly of the outer sealing rim, thus firmly to engage and hold the electrode plate against the patient's skin by a force generated by the vacuum that displaces the back piece, the central portion of the sealing component, and the electrode plate toward the patient's skin upon deformation of the sealing ring portion of the sealing component, and means for restricting the flow of air to the back piece chamber when the electrode is not in place on the patient.

2. An electrode according to claim 1 wherein the means for restricting flow of air to the back piece chamber is a valve means associated with the sealing component for blocking the flow of air in the absence of a force applied to the sealing ring portion of the sealing component.

3. An electrode according to claim 2 wherein the valve means includes an inner sealing rim resiliently engageable with the electrode plate in the absence of an external force applied to the ring portion of the sealing component toward the back piece.

4. An electrode according to claim 3 wherein the central portion of the sealing component, the inner rim of the sealing component and the electrode plate define an intermediate chamber of the electrode, and the central portion of the sealing component has at least one passage communicating the back piece chamber with the intermediate chamber.

5. An electrode according to claim 3 wherein there is at least one hole in the sealing ring portion of the sealing component between the inner sealing rim and the outer sealing rim for communication of vacuum to the zone between the sealing ring portion and the back piece when the electrode is applied to a patient.

6. An electrode according to claim 1 wherein the electrode plate is detachably joined to the back piece.

7. An electrode according to claim 6 wherein the electrode plate is joined to the back piece by a fastener device that includes a stem, and the central portion of the sealing component has a hole adapted to removably receive the stem and to maintain the center portion of the sealing component in a fixed position radially and axially of the stem.

8. An electrode according to claim 7 wherein the fastener device is a snap fastener.

9. An electrode according to claim 1 wherein the sealing ring portion of the sealing component includes an annular rib engageable with the back piece and adapted to be deflected upon displacement of the back piece relative to the ring portion.

10. An electrode according to claim 9 wherein the outer rim of the ring portion of the sealing component includes a substantially rigid annular flange.

11. An electrode according to claim 1 wherein the zone of engagement between the outer sealing rim and the patient's skin is farther from the back piece than is the zone of engagement of the frontal surface of the electrode plate with the patient's skin, whereby the patient's skin is pulled by the vacuum into a convex shape within the outer sealing rim.

12. An electrode according to claim 11 wherein the frontal surface of the electrode plate is concave.

13. An electrode according to claim 12 wherein the frontal surface of the electrode plate has a multiplicity of small protuberances.

14. An electrode according to claim 1 and further comprising a flexible tube connected to the back piece in communication with the back piece chamber and adapted to be connected to a vacuum source and an electrical conductor within the tube connected to the conductive frontal surface of the electrode plate.

15. An electrode according to claim 1 wherein the electrode plate is a portion of an electrode member, the electrode member further including a layer of silver chloride on the frontal surface of the plate portion and a stem portion extending from the back surface, the stem having an enlarged head portion at its distal end, the head being the male element of a snap fastener, and wherein the back piece includes the female element of the snap fastener.

* * * * *